United States Patent
Lamego et al.

(10) Patent No.: US 9,782,077 B2
(45) Date of Patent: Oct. 10, 2017

(54) MODULATED PHYSIOLOGICAL SENSOR

(75) Inventors: Marcelo Lamego, Coto De Caza, CA (US); Cristiano Dalvi, Irvine, CA (US); Hung Vo, Garden Grove, CA (US)

(73) Assignee: Masimo Corporation, Irvine, CA (US)

( * ) Notice: Subject to any disclaimer, the term of this patent is extended or adjusted under 35 U.S.C. 154(b) by 835 days.

(21) Appl. No.: 13/584,447

(22) Filed: Aug. 13, 2012

(65) Prior Publication Data
US 2013/0046204 A1    Feb. 21, 2013

Related U.S. Application Data

(60) Provisional application No. 61/639,985, filed on Apr. 29, 2012, provisional application No. 61/524,744, filed on Aug. 17, 2011.

(51) Int. Cl.
A61B 5/00    (2006.01)

(52) U.S. Cl.
CPC .......... *A61B 5/0051* (2013.01); *A61B 5/4884* (2013.01); *A61B 5/6843* (2013.01); *A61B 2562/0219* (2013.01)

(58) Field of Classification Search
CPC . A61B 5/11; A61B 2562/0219; A61B 5/0051; A61B 5/4884; A61B 5/6843; A61B 7/00
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |

(Continued)

FOREIGN PATENT DOCUMENTS

WO    WO 2009/147615    12/2009

OTHER PUBLICATIONS

US 8,845,543, 09/2014, Diab et al. (withdrawn)
Search Report in Appl. No. GB1214728.6 dated Nov. 29, 2012 in 1 page.

*Primary Examiner* — Daniel Cerioni
*Assistant Examiner* — Yasmeen S Warsi
(74) *Attorney, Agent, or Firm* — Knobbe Martens Olson & Bear, LLP

(57) ABSTRACT

A modulated physiological sensor is a noninvasive device responsive to a physiological reaction of a living being to an internal or external perturbation that propagates to a skin surface area. The modulated physiological sensor has a detector configured to generate a signal responsive to the physiological reaction. A modulator varies the coupling of the detector to the skin so as to at least intermittently maximize the detector signal. A monitor controls the modulator and receives an effectively amplified detector signal, which is processed to calculate a physiological parameter indicative of the physiological reaction.

8 Claims, 10 Drawing Sheets

(56) References Cited

U.S. PATENT DOCUMENTS

| | | |
|---|---|---|
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |

(56) References Cited

U.S. PATENT DOCUMENTS

| | | |
|---|---|---|
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |

(56) References Cited

U.S. PATENT DOCUMENTS

| | | |
|---|---|---|
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |

(56) References Cited

U.S. PATENT DOCUMENTS

| | | |
|---|---|---|
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 2004/0034289 A1* | 2/2004 | Teller et al. ............. 600/300 |
| 2007/0096911 A1 | 5/2007 | Gualtieri |
| 2007/0100666 A1* | 5/2007 | Stivoric et al. ............. 705/3 |
| 2008/0086063 A1* | 4/2008 | Baxter et al. ............. 601/46 |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |

(56) References Cited

U.S. PATENT DOCUMENTS

| | | |
|---|---|---|
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |

\* cited by examiner

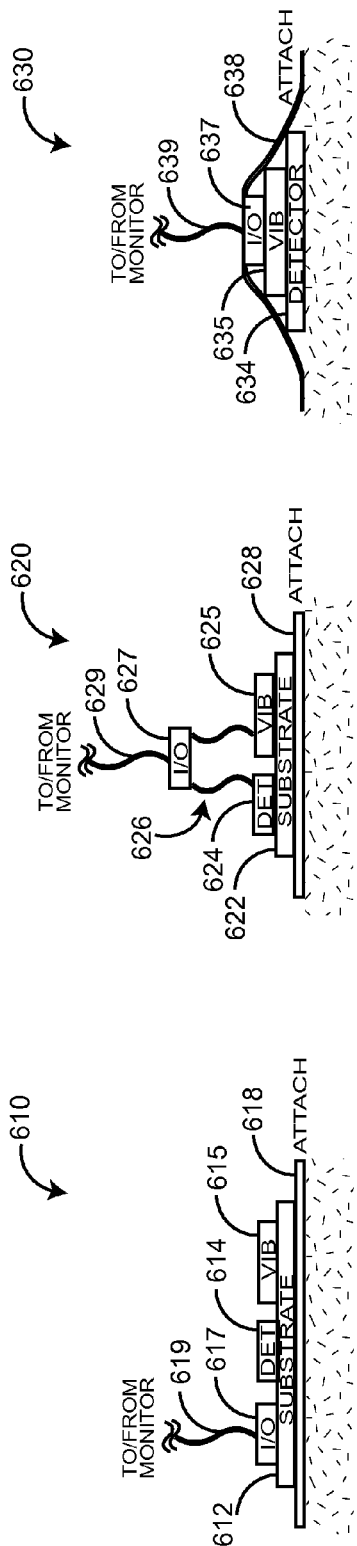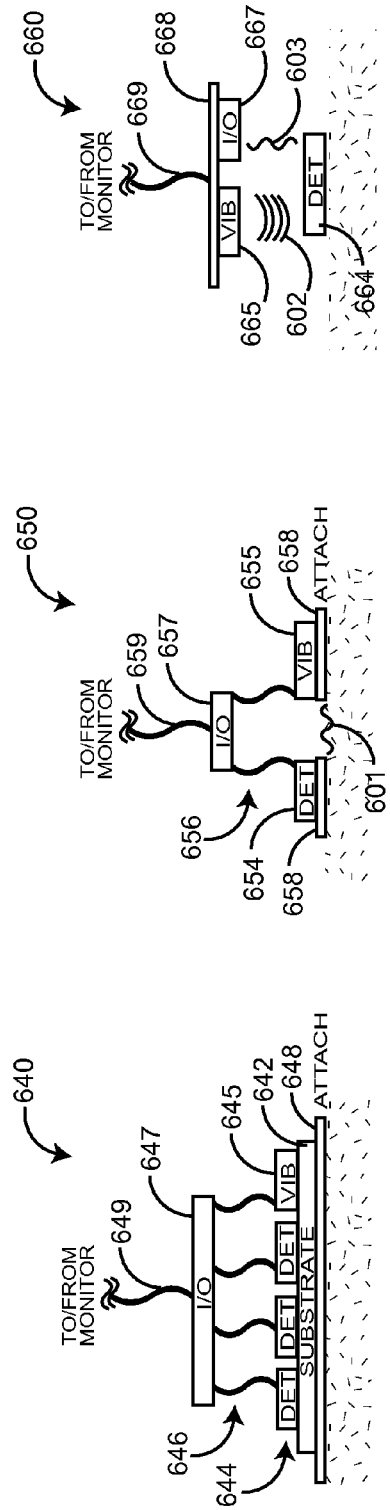

MODULATED PHYSIOLOGICAL SENSOR

CROSS-REFERENCE TO RELATED APPLICATIONS

The present application claims priority benefit under 35 U.S.C. §119(e) to U.S. Provisional Patent Application Ser. No. 61/524,744, filed Aug. 17, 2011, titled Modulating Physiological Sensor and U.S. Provisional Patent Application Ser. No. 61/639,985, filed Apr. 29, 2012, titled Modulated Physiological Sensor, both provisional applications hereby incorporated in their entirety by reference herein.

BACKGROUND OF THE INVENTION

From a physiological perspective, the human body comprises a set of interacting systems, each having specific functions and purposes. These systems maintain the body's internal stability by coordinating the response of its parts to any situation or stimulus that would tend to disturb its normal condition or function. The nervous system includes the central nervous system and the peripheral nervous system. The central nervous system is the brain and the spinal cord. The musculoskeletal system includes the skeleton and attached muscles and includes bones, ligaments, tendons, and cartilage. The circulatory system includes the heart and blood vessels, including arteries, veins and capillaries. The respiratory system includes the nose, trachea and lungs. The gastrointestinal system includes the mouth, esophagus, stomach, intestines, liver, pancreas and gallbladder. The integumentary system includes the skin, hair, nails, sweat glands and sebaceous glands. The urinary system includes the kidneys and bladder. The immune system includes white blood cells, thymus and lymph nodes. The endocrine system includes the pituitary, thyroid, adrenal and parathyroid glands.

Various sensors may be applied for analyzing and measuring the processes occurring in the above-cited physiological systems and for generating physiological parameters indicative of health or wellness as a result. As one example, a pulse oximetry sensor generates a blood-volume plethysmograph waveform from which oxygen saturation of arterial blood and pulse rate may be determined, among other parameters. As another example, an acoustic sensor may be used to detect airflow sounds in the lungs, bronchia or trachea, which are indicative of respiration rate.

SUMMARY OF THE INVENTION

The physiological systems cited above maintain the stability, balance and equilibrium of a living being. Modulation may be advantageously used to accentuate detection of processes occurring within these physiological systems. An example of natural modulation is tissue vibration in the trachea due to the inflow and outflow of air between the lungs and the nose and mouth. This vibration creates sound waves at a higher frequency than the underlying respiration. An acoustic sensor utilizing a piezoelectric device attached to the neck is capable of detecting these sound waves and outputting a modulated sound wave envelope that can be demodulated so as to derive respiration rate. An acoustic respiration rate sensor and corresponding sensor processor is described in U.S. patent application Ser. No. 12/904,789, filed Oct. 14, 2010, titled Acoustic Respiratory Monitoring Systems and Methods, assigned to Masimo Corporation, Irvine, Calif. ("Masimo") and incorporated by reference herein.

Another example of natural modulation is pulsatile arterial blood flow at a peripheral tissue site, such as a fingertip, resulting from pressure waves generated by the heart. An optical sensor generates a plethysmograph waveform responding to changes in a light absorption due to the pulsatile blood flow so as to measure blood composition, such as hemoglobin constituents. This plethysmograph also modulates a respiration envelope that can be demodulated so as to derive respiration rate.

An example of artificial modulation is a physiological sensor having an accelerometer and a vibration element mounted on a substrate so that the vibration element is in mechanical communications with the accelerometer. An interface communicates at least one axis of the accelerometer signal to a monitor. The substrate is attached to the skin surface of a living being, and the vibration element is activated so as to modulate the skin surface coupling at a modulation frequency. In an embodiment, an artificially-modulated sensor is responsive to respiratory-induced movements at the skin surface.

One aspect of a modulated physiological sensor is a noninvasive sensor responsive to a physiological reaction of a living being to an internal or external perturbation that propagates to a surface area of the living being. The modulated physiological sensor has a detector configured to communicate with a surface area of a living being so as to generate a signal responsive to a physiological reaction of the living being to the perturbation. A modulator varies the coupling of the detector to the surface area so as to at least intermittently maximize the detector signal. A monitor controls the modulator and receives a detector signal so as to calculate a physiological parameter indicative of a physiological state of the living being.

In various embodiments, the modulator is a vibration element that mechanically accentuates the coupling of the detector to the surface area. A substrate co-mounts the detector and the vibration element. An attachment releasably affixes the substrate, detector and vibration element to the surface area. In an embodiment, the detector is an accelerometer and the vibration element is a coin motor. The substrate is a circuit board that mechanically mounts and electrically interconnects the accelerometer and coin motor. The attachment is a tape having a sticky side that attaches to the surface area and a housing side that encloses the circuit board.

Another aspect of a modulated physiological sensor is a sensing method the provides a detector responsive to a physiological wave generated within a living being that propagates to a skin surface and couples the detector to the skin surface. The detector coupling is modulated so as to generate a modulated detector output indicative of the physiological wave. The detector signal is demodulated so as to derive a physiological signal, and a physiological parameter is determined from the physiological signal. In various embodiments, the modulation is vibration of the detector by co-mounting the detector and a vibration element. The detector and the vibration element may be co-mounted to a common substrate, which is attached to the skin surface. A second detector and a second vibration element may be mounted to the common substrate and isolated from the combination detector and vibration element.

A further aspect of a modulated physiological sensor is a detector means for responding to physiological propagations reaching a skin surface of a living being and a modulator means for varying the coupling of the detector means to the skin surface. A monitor demodulates a sensor signal from the detector means so as to analyze the physiological propagations and generate a physiological parameter output. In various embodiments, a substrate means mounts the detector means and the modulator means and an attachment means secures the substrate to the skin surface. A control signal from the monitor sets a frequency of the modulator means above a low frequency cutoff of the detector means. In an embodiment, the modulator means is a vibration element, the detector means is multiple detectors, the modulator means is multiple vibration elements and the substrate means incorporates at least one isolation element so as to isolate detector and vibration element pairs. In an embodiment, the vibration element remotely modulates the detector via an acoustic wave.

BRIEF DESCRIPTION OF THE DRAWINGS

FIGS. 6A-F are side views of various modulated physiological sensor embodiments;

DETAILED DESCRIPTION OF THE PREFERRED EMBODIMENTS

Figure 1:
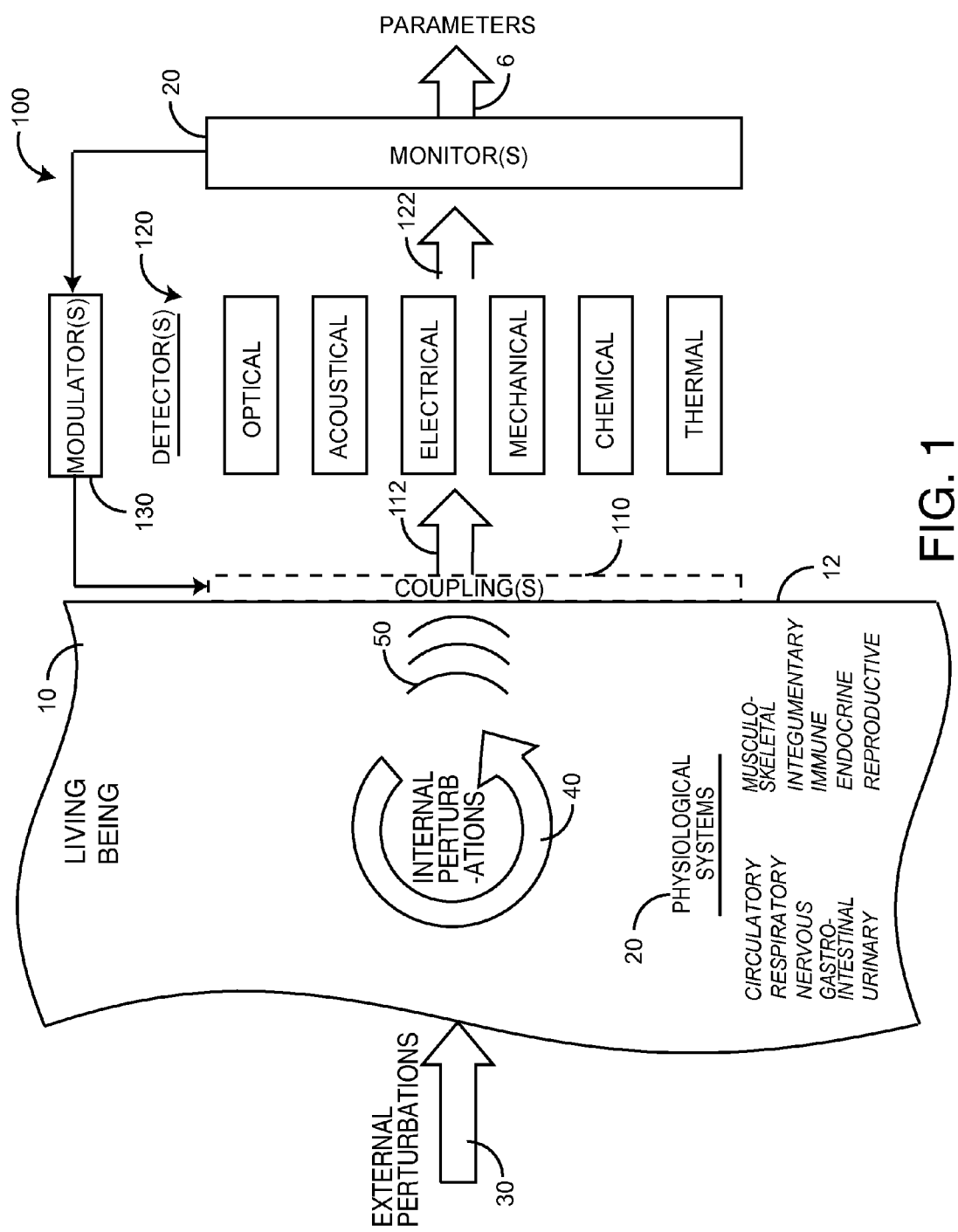
FIG. 1 is a general block diagram of a modulated physiological sensor in communications with the physiological systems of a living being.

FIG. 1 generally illustrates a modulated physiological sensor 100 in communications with the physiological systems 20 of a living being 10. Physiological reactions 50 to external 30 or internal 40 perturbations propagate to the body surface 12 and are coupled 110 to one or more detectors 120. These physiological reactions 50 are indicative of states and processes of the physiological systems 20. The detectors 120 are responsive to coupled physiological reactions 112 so as to generate detector outputs 122. One or more monitors 20 are responsive to the detector outputs 122 so as to compute physiological parameters 6 that quantify the states and processes of the physiological systems 20. The coupling(s) 110 is advantageously modulated 130 under control of the monitor(s) 20 so as to accentuate detection of the physiological reactions 50, as described in further detail below.

As shown in FIG. 1, detectors 120 include any device that is responsive to the coupled physiological reactions 112 such as optical, acoustical, electrical, mechanical, chemical and thermal mechanisms, to name a few. The detector outputs 122 may include blood photo-plethysmographs, ECG, EEG and body sound waveforms; indications of skin color, temperature, movement or pressure; and chemical responses and measurements of moisture, breath, sweat or odors, to name a few. The monitor(s) 20 may include any or all devices or combinations of devices that are responsive to the detector outputs 122 alone or in combination so as to calculate or otherwise derive physiological parameters 6 that measure, graph, quantify or otherwise indicate one or more aspects of the physiological systems 20 and corresponding states and processes corresponding to the physiological reactions 50. Parameter examples include circulatory system measurements such as oxygen saturation, heart rate, blood glucose and blood pressure; and respiratory system measurements such as respiration rate and volume, to name but a few. Parameters 6 can also include indications of specific abnormal physiological conditions such as sleep apnea, anemia and hypoglycemia, to name a few.

Also shown in FIG. 1, external perturbations 30 may be natural, such as changes to a person's physical environment including temperature, pressure, light and sound, for example. External perturbations 30 also may be artificial, such as the mechanical pressure induced by a respirator for breathing assistance or by a pulser on a fingertip for measuring venous oxygen saturation as examples. Internal perturbations 40 include normal and abnormal functioning and interactions of various physiological systems 20, including circulatory and respiratory functions, to name a few. Internal perturbations 40 may also be artificial, such as due to a pacemaker or other implanted device. Physiological reactions 50 resulting from external perturbations 30 or internal perturbations 40 include, as examples, a body surface expansion or contraction due to, say, lung inflation/deflation; an acoustic wave arriving from within the body to the body surface due to a heart beat or bowel sound; or a transverse wave traveling along the body surface due to a muscle spasm. In general a physiological reaction 50 may be an optical, acoustical, electrical, mechanical, chemical or thermal impulse, wave or other variation or change. Further, external perturbations 30 or internal perturbations 40 need not be the same type or kind (e.g. optical, acoustical, electrical, mechanical, chemical or thermal) as the corresponding physiological reaction 50 or the detector element 120 responsive to the physiological reaction 50. For example, an injection (external chemical perturbation) may trigger a heart arrhythmia that results in an acoustic and a mechanical wave (physiological reaction) that propagates to the skin surface and is detected by an acoustical or mechanical sensor, or both. Further, the heart arrhythmia may result in an arterial pulse abnormality that changes the optical characteristics of a tissue site as measured by an optical sensor attached to the tissue site.

Figure 2:
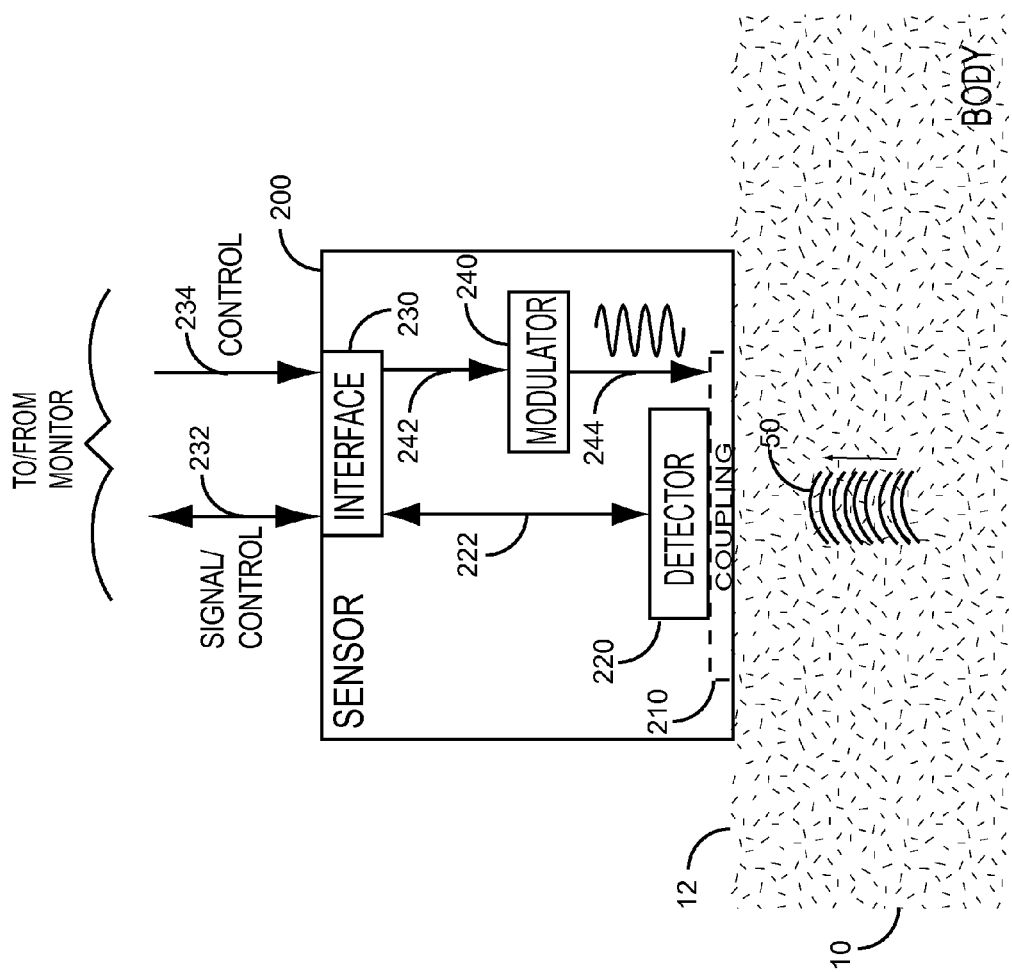
FIG. 2 is general block diagram of a modulated physiological sensor embodiment.

FIG. 2 illustrates a modulated physiological sensor 200 embodiment that attaches to a body surface 12 and is configured to respond to physiological reactions 50, as described above. The sensor 200 has a coupling 210, a detector 220, an interface 230 and a modulator 240. A monitor (not shown) outputs controls 232, 234 to the sensor 200 and receives signals 232 from the sensor 200. The interface 230 communicates detector signals 222 to the monitor in response to drive controls 222 to the detector 220. The interface 230 also communicates a modulator control 242 to the modulator 240. The modulator 240 responds to the modulator control 242 so as to generate a modulation 244 to the coupling 210.

As shown in FIG. 2, the modulator 240 varies the coupling 210 of the detector 220 to the body surface 12 and hence to the physiological reaction 50. In particular, the body surface 12 of a person, including skin and underlying tissues, varies by individual and, indeed, by location on a particular individual. These variations are in shape, texture, color and elasticity to name a few. As such, a fixed coupling is unlikely to provide an optimum body surface/detector interface. Indeed efficient and effective body surface/detector coupling is an issue for most if not all physiological sensors. For example, common ECG electrodes require a conductive gel so as to effectively couple to a skin surface. The modulator 240 advantageously continuously varies the detector coupling 210 to the skin surface across a range of contact forces at the skin/sensor interface. For an electrical detector, say, this varied coupling alters the detector electrical resistance at the skin surface over a range of values. For a mechanical detector, the varied coupling alters the mechanical impedance of the detector at the skin surface over a range of values. For an acoustic detector, for example, the varied coupling alters the acoustical impedance of the detector at the skin surface over a range of values. As a result of this variable detector coupling to the skin surface, the detector has maximal and minimal coupling each modulation cycle. Further, the modulation frequency may be set above any detector low frequency response cutoffs. Accordingly, the modulation advantageously amplifies the detector signal 222, as described in further detail with respect to FIGS. 3A-D, below.

Figure 3B:
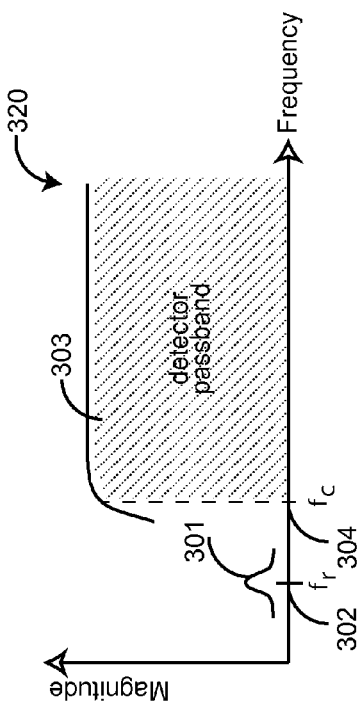
FIGS. 3A-D are amplitude vs. time and corresponding amplitude vs. frequency graphs of a physiological reaction and a corresponding modulated and detected reaction.
Figure 3D:
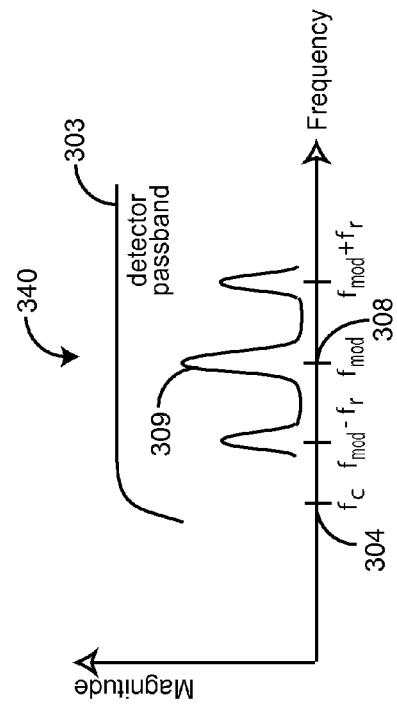
Figure 3A:
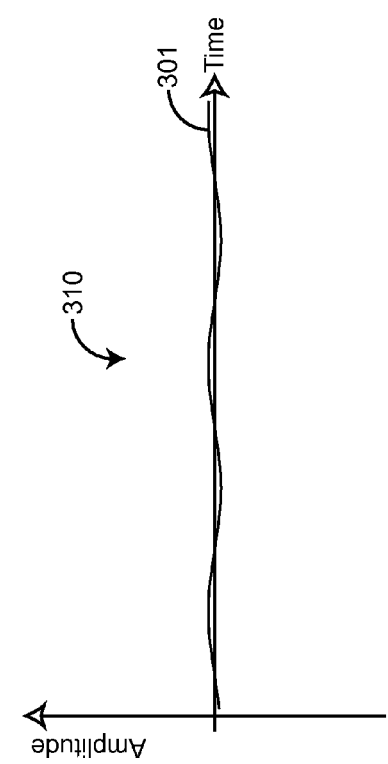

FIGS. 3A-D illustrate a physiological system reaction to perturbations and a corresponding modulated and detected sensing of the reaction. FIG. 3A is an exemplar time domain graph 310 of a relatively low amplitude, low frequency physiological system reaction 301 to some form of internal or external perturbation. FIG. 3B is a corresponding exemplar frequency domain graph 320 of the physiological system reaction 301. The physiological reaction 301 may be difficult to detect due to either a small amplitude signal 301 or a signal frequency $f_r$ 302 less than the detector cutoff frequency $f_c$ 304, i.e. outside the detector passband 303.

Figure 3C:
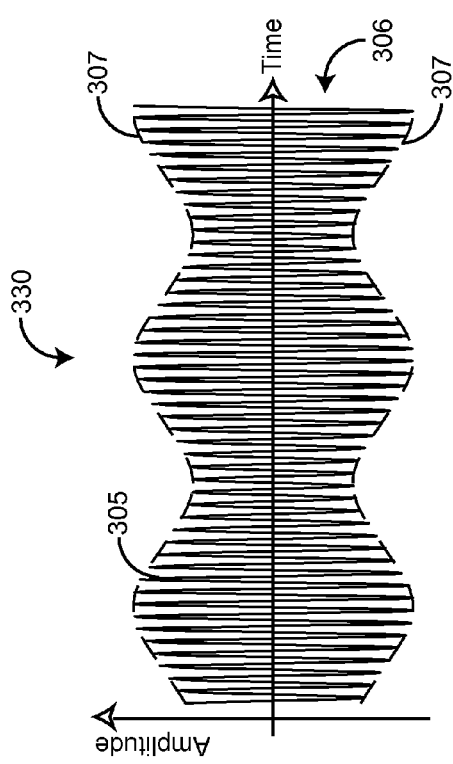

FIG. 3C is an exemplar time domain graph 330 of a modulated detector response 305 to the reaction 301 (FIG. 3A) described above. The response 305 has a modulation 306 and an envelope 307. In particular, the physiological sensor 200 (FIG. 2) has a modulated coupling 210 (FIG. 2) that achieves or approaches a maximal coupling of a detector 220 (FIG. 2) to a body surface 12 (FIG. 2) at least once per modulation cycle, as described with respect to FIG. 2 above. Accordingly, the modulated detector 220 (FIG. 2) accentuates the physiological signal 301 (FIG. 3A) during the maximal coupling and de-accentuates the physiological signal 301 (FIG. 3A) during the minimal coupling. This cyclical accentuation/de-accentuation generates an envelop 307 that is, effectively, an amplification of the physiological reaction 301 (FIG. 3A).

FIG. 3D is an exemplar frequency domain graph 340 of a modulated physiological sensor response 305 (FIG. 3C). In various embodiments, the modulation frequency $f_{mod}$ 308 is set substantially higher than any low frequency cutoff $f_c$ 304 of the detector so that the sensor response 305 is well within the detector passband 303 (FIG. 3B).

As described with respect to FIGS. 3A-D, in various embodiments an amplified version of the physiological response 301 (FIG. 3A) is derived from the sensor response 305 (FIG. 3C) by any of various well-known AM demodulation techniques. These include envelope detection with a rectifier or product detection utilizing multiplication by a local oscillator, to name a few.

Figure 4:
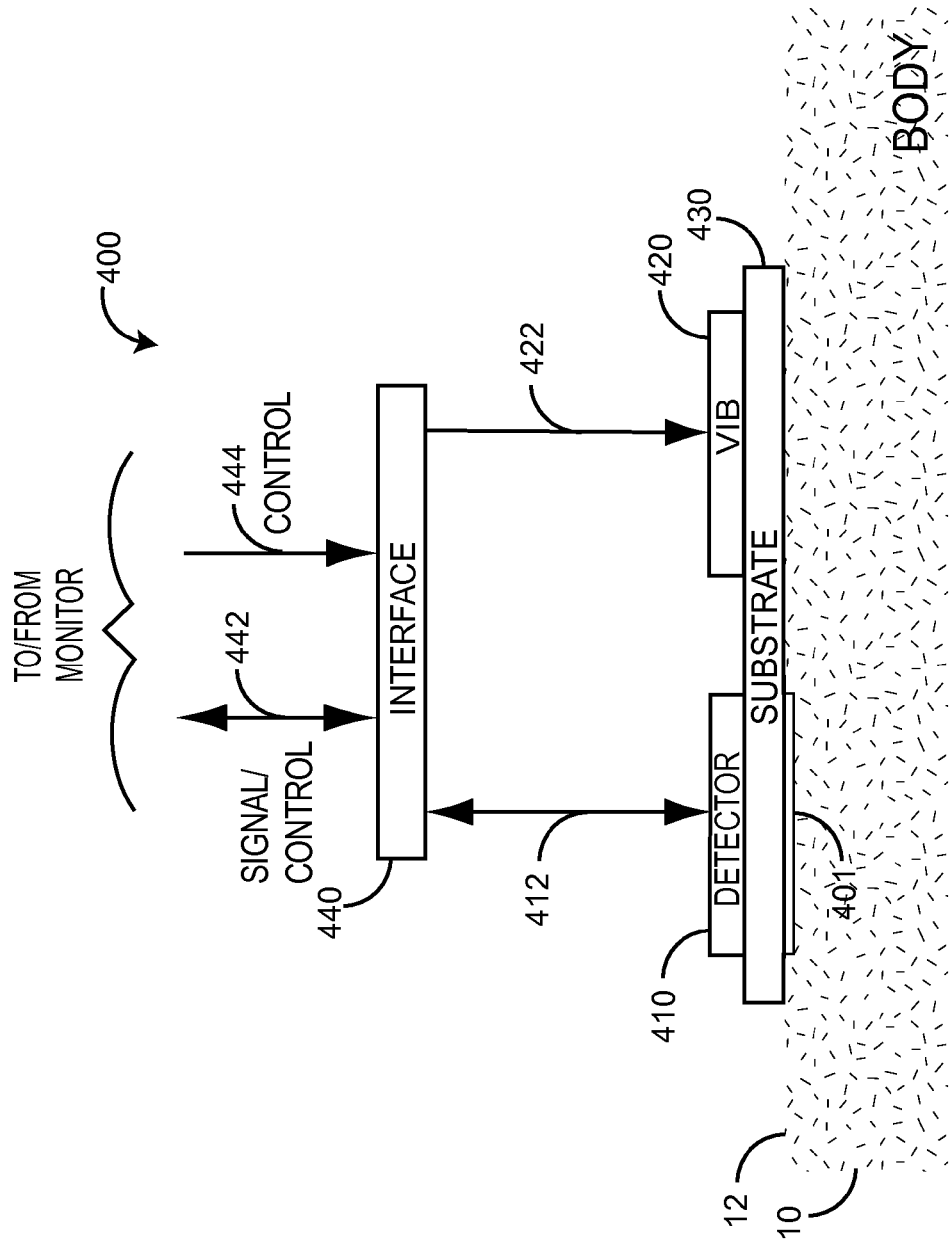
FIG. 4 is a general block diagram of a vibration-modulated physiological sensor embodiment.

FIG. 4 illustrates a vibration-modulated physiological sensor 400 embodiment. The sensor 400 has a detector 410, a vibration element ("vib") 420, a substrate 430 and an interface 440 to a monitor. The detector 410 and the vib 420 are both mounted to the substrate 430. In an embodiment, the detector 410 is mounted so as to directly couple 401 to the body surface 12. For example, the detector 410 may be mounted through the substrate 430, as shown. In other embodiments, the detector 410 is attached adjacent the substrate 430. In additional embodiments, the detector 410 may not contact the body surface 12 at all, such as with an accelerometer-based detector described with respect to FIGS. 7-10, below. In an embodiment, the vib 420 is a coin motor, as described with respect to FIGS. 7-10, below. In other embodiments, the vib 420 is any of various off-balance motors, voice coils or similar electro-mechanical devices. In further embodiments, the vib 420 is any mechanical, electromagnetic, piezoelectric, pneumatic, electric, acoustic or magnetic device that vibrates in response to an electrical signal.

As shown in FIG. 4, the detector 410, and hence the coupling 401, is vibration-modulated 420 via the substrate 430. The substrate 430 may be any material that effectively transmits or conducts vibrations from the vib 420 to the detector 401. In an advantageous embodiment, the substrate 430 is a circuit board material that provides mechanical mounts for and supports electrical interconnects between the sensor components.

Also shown in FIG. 4, a monitor (not shown) outputs controls 442, 444 to the sensor 400 and receives signals 442 from the sensor 400. The interface 440 communicates detector signals 412 to the monitor in response to drive controls 412 to the detector 410. The interface 440 also communicates a vibration control 422 to the vib 420. The vib 420 responds to the vibration control 422 so as to generate a modulation to the coupling 401 via the substrate 430. In various embodiments, the detector 410 may be mechanical, such as an accelerometer described with respect to FIGS. 7-10, below. In other embodiments, the detector 410 may be electrical, such as an electrode for sensing ECG or EEG signals; or optical such as a photodiode; or acoustical, such as a piezoelectric device; or thermal, such as a thermopile, pyrometer, thermistor, thermocouple, IR photodiode or temperature diode, to name a few.

Figure 5:
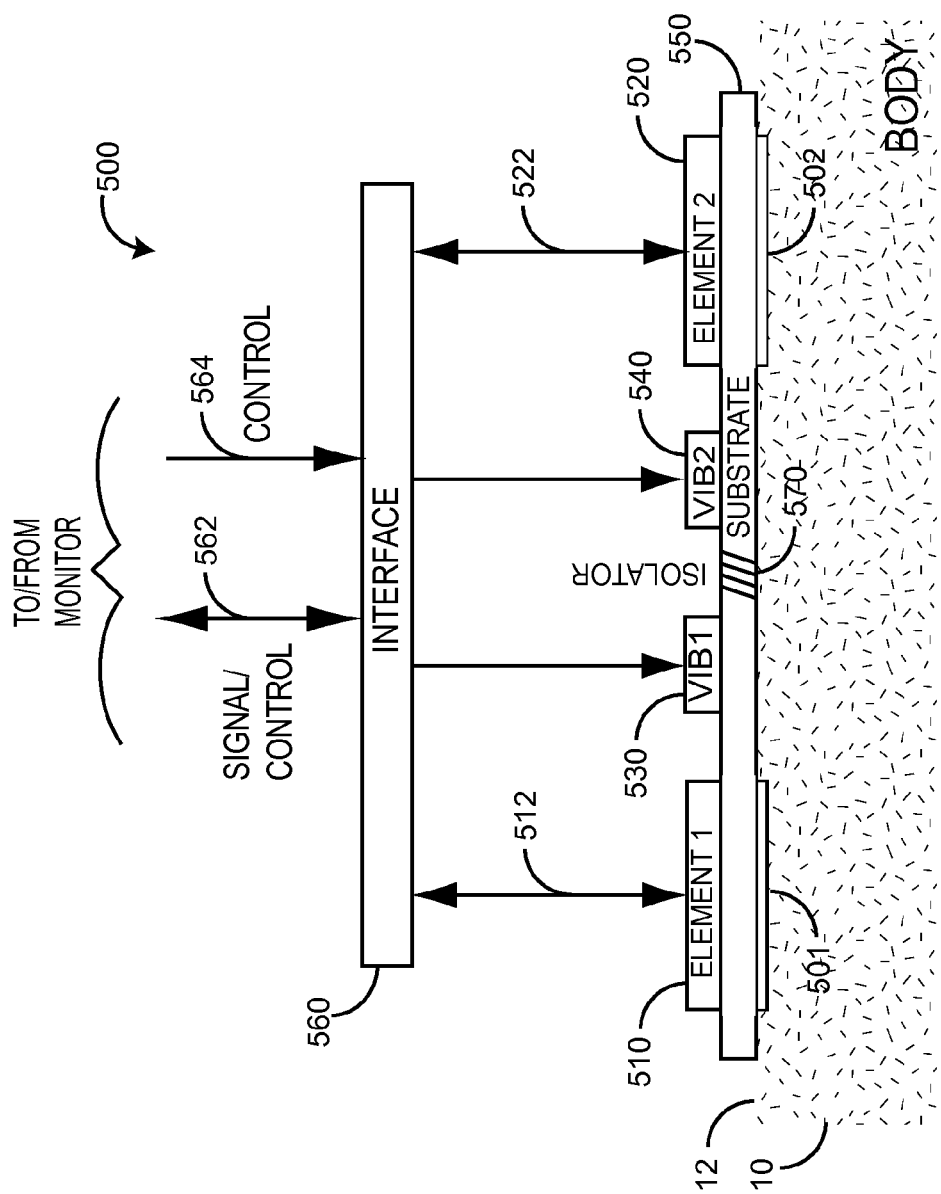
FIG. 5 is a general block diagram of a multi-element, vibration-modulated sensor embodiment.

FIG. 5 illustrates a multiple-element, vibration-modulated sensor 500 embodiment having a two or more sensor elements 510, 520, one or more vibration elements (vibs) 530, 540, a substrate 550 and an interface 560 to a monitor. The sensor elements 510, 520 may each be detectors or a combination of one or more detectors and one or more emitters. In an embodiment, the sensor elements 510, 520 are different types of detectors. For example, element1 510 may be mechanical and element2 may be electrical. In an embodiment, the sensor elements 510, 520 may be an emitter and a corresponding detector. For example, element1 510 may be an LED for illuminating a tissue site and element2 520 may be a optical detector, such as a diode or diode array, for receiving the LED illumination after attenuation by the tissue site. Advantageously, multiple elements 510, 520 on a single substrate 550 provide an array of like sensors for increased detection capability or for directional sensing capability, such as determining the source of a body sound as but one example. Advantageously, multiple elements 510, 520 on a single substrate 550 provide an array of different sensors in a single sensor package for simultaneous detection and analyses of multiple types or kinds of physiological responses to the same or different external or internal perturbations.

As shown in FIG. 5, multiple vibs 530, 540 may be separated by a substrate isolator 570. In this manner, vib1

530 solely effects the coupling 501 of element1 510 to a body surface 12 and, likewise, vib2 540 solely effects the coupling 502 of element2 520 to a body surface 12. Multiple isolated vibs 530, 540 advantageously allow each vib 530, 540 output to be adapted or otherwise suited to a particular element 510, 520, both in terms of amplitude and frequency. In an embodiment, the isolator 570 is a material that significantly attenuates mechanical/acoustical waves at the vib frequency or frequencies.

Also shown in FIG. 5, a monitor (not shown) outputs controls 562 to the sensor 500 and receives signals 562 from the sensor 500. The interface 560 communicates element signals 512, 522 to the monitor in response to drive controls 512, 522 to the elements 510, 520. The interface 560 also communicates vibration (vib) controls 564 to the vibs 530, 540. The vibs 530, 540 respond to the vib controls 564 so as to generate a modulation to their respect couplings 501, 502.

FIGS. 6A-F illustrate various modulated physiological sensor configurations. As shown in FIG. 6A, an integrated sensor embodiment 610 has a substrate 612, a detector 614, a vibration element (vib) 615, I/O (input/output) 617, an attachment 618 and electrical communication 619 to a monitor or similar device (not shown). The substrate 612 mounts the detector 614, vib 615 and I/O 617. In an embodiment, the substrate 612 also provides electrical trace interconnects between the I/O and both the detector 614 and vib 615. The I/O 617 transmits/receives sensor signals/controls and, in particular, drive to the vib 615 and signals from the detector 614. The attachment 618 adheres the substrate 612 and mounted components 614-617 to a body surface. In an embodiment, the detector 614 is mounted through the substrate 612 so as to couple directly to a body surface or via the attachment 618. The vib 615 advantageously modulates the coupling of the detector 614 to the body surface via the substrate 612 on which the detector 614 and vib 615 are co-mounted.

As shown in FIG. 6B, a semi-integrated sensor embodiment 620 has a substrate 622, a detector 624, a vib 625, I/O 627, an attachment 628 and electrical communication 629 to/from a monitor or other control or display device. The semi-integrated sensor embodiment 620 is similar to the integrated sensor embodiment 610 except that the I/O 627 is external to the sensor 620 and may be mounted in the monitor (not shown) or in a pod (not shown) between the sensor 620 and monitor. The I/O 627 is in electrical communications 626 with the detector 624 and vib 625, such as via cabling or other interconnect technology. The I/O 627 is also in electrical communications 629 with a monitor.

As shown in FIG. 6C, a substrate-less sensor embodiment 630 has a detector 634, a vib 635, I/O 637, an attachment 638 and electrical communications 639, which transmits signals and controls between the I/O 637 and a monitor or similar device (not shown). In this embodiment, the detector 634 or more specifically the detector package, such as a chip carrier, substitutes for a substrate. Accordingly, the vib 635 and I/O 637 are mounted within or on or otherwise directly coupled to the detector 634 package so that the detector 634 package is directly coupled to the body surface and held in place with the attachment 638. In an embodiment, the attachment 638 is simply an adhesive layer on the detector 634 package.

As shown in FIG. 6D, a sensor array embodiment 640 has a substrate 642, multiple detectors 644, a vib 645, I/O 647, an attachment 648 and electrical communication 649. The sensor array embodiment 640 is similar to the semi-integrated embodiment 620 (FIG. 6B) except for the multiple detectors 644. The detectors 644 may be all the same device type (mechanical, electrical, acoustical, etc.), all different or a mixture of one or more sub-arrays of the same device type with one or more different device types. Advantageously, multiple detectors 644 on a single substrate 642 provide an array of like sensors for increased detection capability or for directional sensing capability, such as determining the source of a body sound. Advantageously, multiple detectors 644 on a single substrate 642 provide an array of different detectors in a single sensor package for simultaneous detection and analyses of multiple types or kinds of physiological responses to the same or different external or internal perturbations. Advantageously, a mix of detectors and transmitters (not shown), such as one or more LEDs and one or more photodiode detectors, provide active sensing capabilities, such as illuminating and analyzing arterial (pulsatile) blood flow. Advantageously, one or more vibs 645 may provide both modulation and an active pulse for, say, analyzing non-pulsatile (venous) blood flow, as but one example.

As shown in FIG. 6E, a non-integrated sensor embodiment 650 has a detector 654, a vib 655 and attachments 658. The detector 654 and vib 655 are separately attached 658 to a body surface. The I/O 657 is in electrical communications 656 with the detector 654 and vib 655, such as via cabling or other interconnect technology, including wireless. Further, the I/O 657 is external to the sensor 650 and may be mounted in the monitor (not shown) or in a pod (not shown) between the sensor 650 and monitor with electrical communications 659 between the I/O 657 and the monitor. Advantageously, the vib 655 is attached to the body surface in close proximity to the detector 654 so that surface waves 601 generated by the vib in the body modulate the coupling between the detector 654 and the body surface.

As shown in FIG. 6F, a remote sensor embodiment 660 has a detector 664 and a modulation module 665. The modulation module 668 has a vib 665 and I/O 667. Advantageously, the vib 665 remotely modulates the detector 664 when brought into proximity to the detector 664. In particular, the vib 665 generates an acoustic wave 602 that vibrates the detector so as to modulate the detector coupling to the body surface. In particular, the acoustic wave 602 propagates through media intervening between the vib 665 and the detector 664. That media may be an air gap when the module 668 is positioned immediately over the detector 664 or the media may be tissue when the module 668 is positioned immediately over or on the body surface proximate the detector 664.

Figure 7:
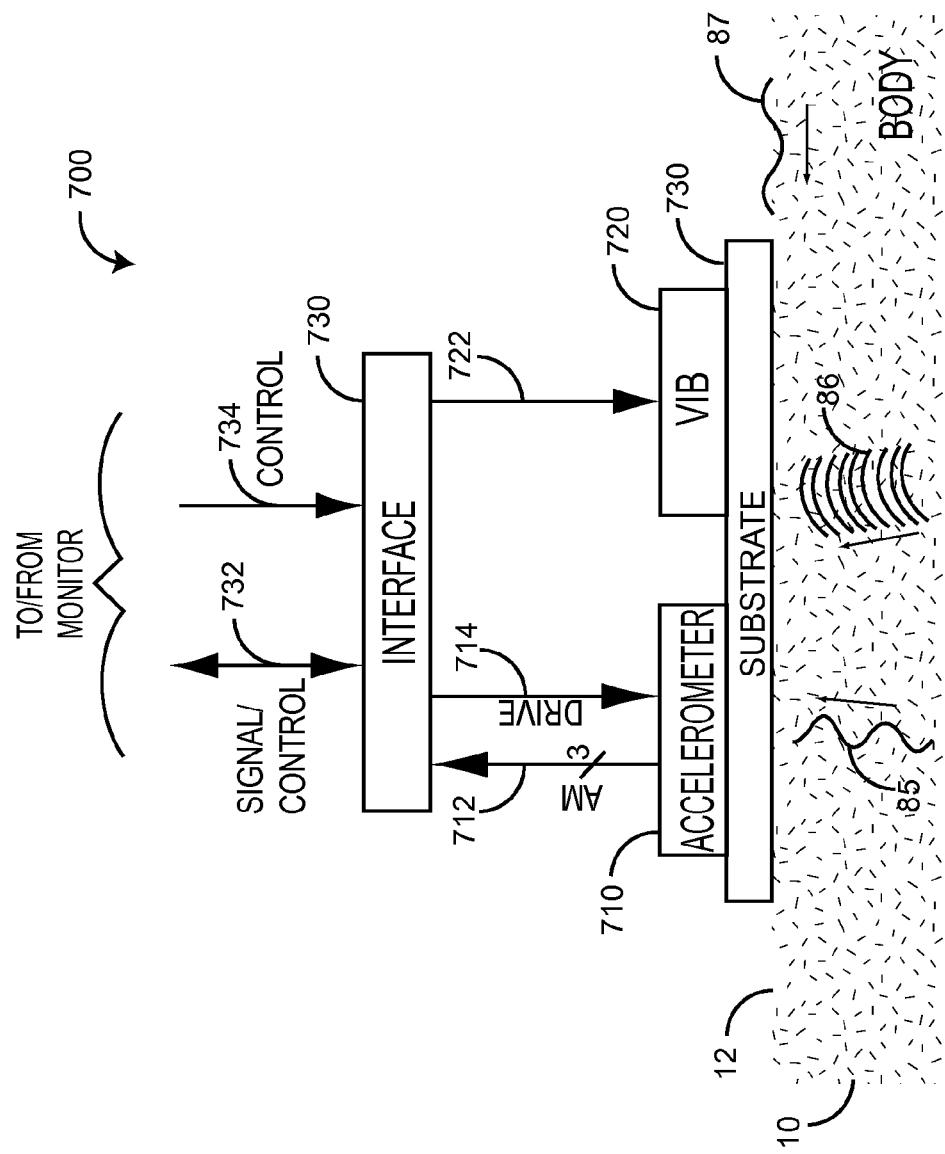
FIG. 7 is a general block diagram of a vibration-accelerometer physiological sensor embodiment.

FIG. 7 generally illustrates a modulated physiological sensor 700 embodiment having an accelerometer 710 and a vibration element (vib) 720 mounted on a common substrate 730. An attachment (not shown) adheres or otherwise couples the substrate 730 to a body surface 12. The accelerometer 710 has three outputs 712 responsive to accelerations in three dimensions (x, y, z) advantageously enabling the sensor 700 to detect both the amplitude, direction and/or type of propagations (translational 85, 87 and longitudinal 86, 88) and whether the propagations are body waves 85, 86 or surface waves 87. The vib 720 mechanically modulates the coupling of the substrate 730 and, accordingly, the coupling of the accelerometer 710 to the body surface 12. The vib 720 frequency is selected to be substantially higher than the frequency of the propagations 85-88. As such, the accelerometer x, y and z outputs 712 are each amplitude modulated (AM) representations of the propagations 85-87. Advantageously, the modulated coupling substantially amplifies the propagations due to a peak AC coupling occurring once every cycle of the vib. That peak AC coupling is substantially greater than can be practically achieved with any static coupling of the accelerometer to the body surface 12. Accordingly, very low amplitude propagations can be detected and measured to yield physiological parameters. See, for example, a respiration rate sensor described with respect to FIGS. 8-10, below.

Figure 8:
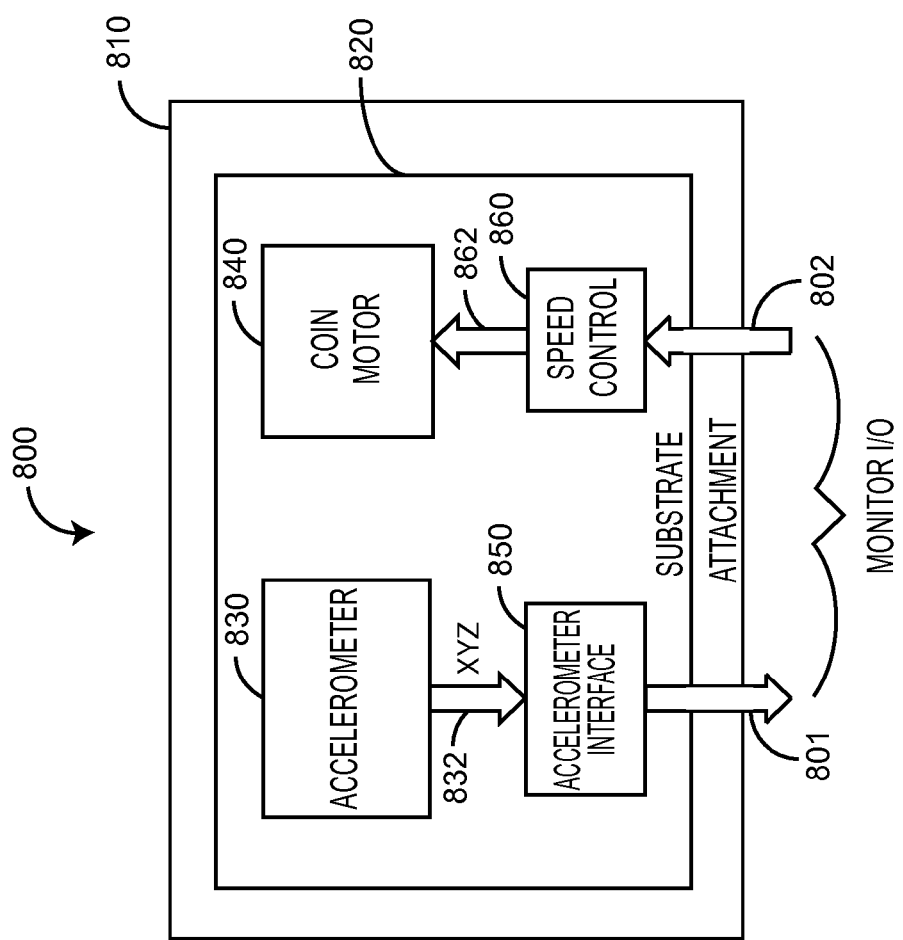
FIG. 8 is a detailed block diagram of a vibration-accelerometer physiological sensor embodiment.
Figure 9:
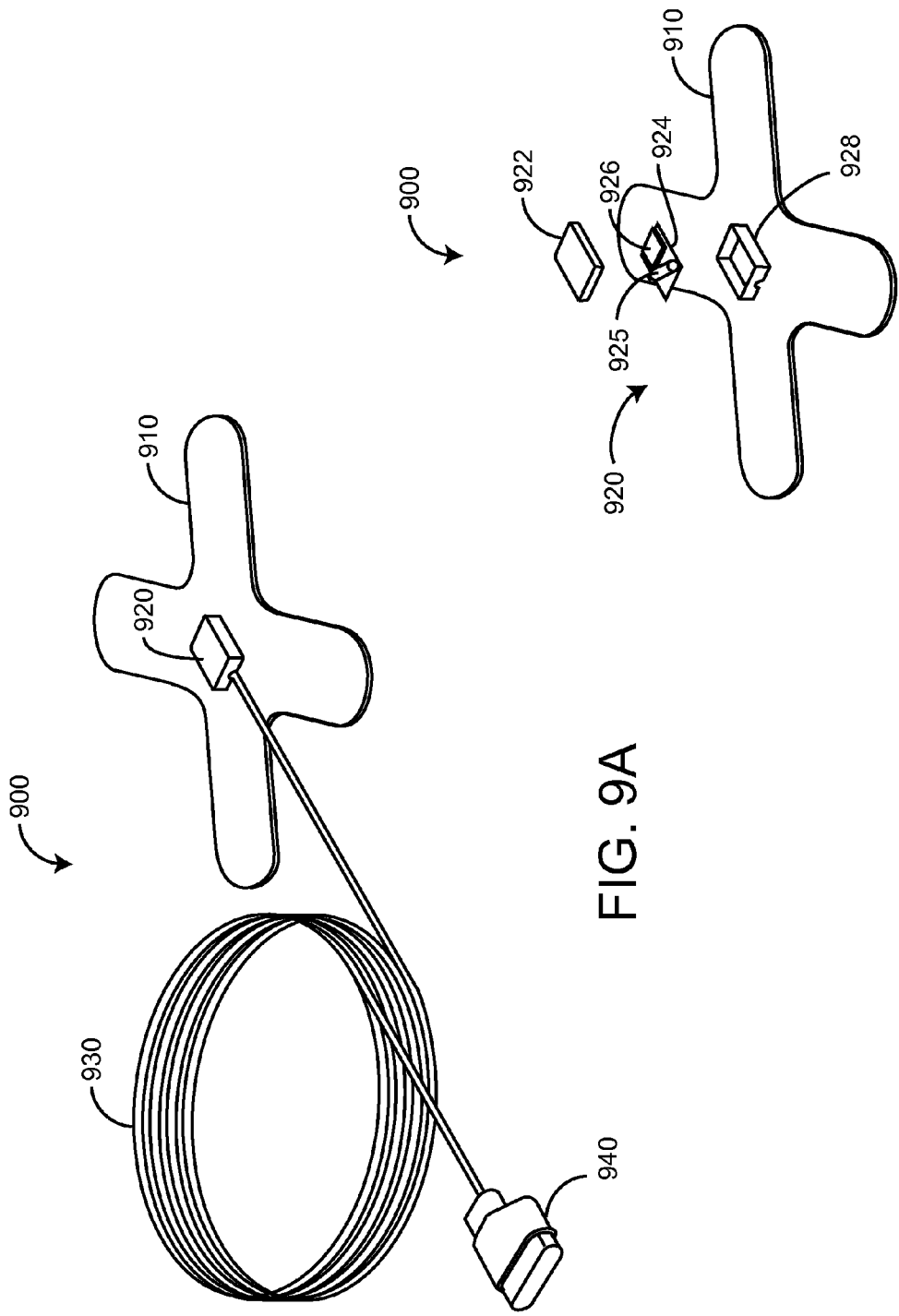
FIG. 9A-B are assembled and exploded perspective views, respectively, of a vibration-accelerometer physiological sensor embodiment.

FIG. 8 is a detailed block diagram of a vibration-modulated physiological sensor 800 embodiment. The sensor 800 has an attachment 810, a substrate 820, an accelerometer 830, a coin motor 840 that generates vibration modulation, an accelerometer interface 850, a speed control 860 and monitor inputs/outputs (I/O) 801, 802. In an embodiment, the accelerometer 830 is an LIS352AX±2 g full scale, analog output, 3-axis (X, Y and Z) linear accelerometer available from STMicroelectronics, Geneva, Switzerland. In an embodiment, the coin motor 840 is a 10 mm coin motor 310-101 available from Precision Microdrives Ltd., London, UK. In an embodiment, the substrate 820 is a circuit board material that mechanically mounts and electrically interconnects the accelerometer 830, the coin motor 840, the accelerometer interface 850 and the speed control 860. In an embodiment, the attachment 810 is a sticky tape that mounts the sensor 800 to a body surface of a living being. In an embodiment, the monitor I/O 802 to the speed control is via a I$^2$C bus. In an embodiment, the monitor I/O 801 to the accelerometer 830 includes a multiplexer control input to the accelerometer 830 to select one of the X, Y and Z axis for the accelerometer output 832 to the monitor. In another embodiment, all of X, Y and Z axes are simultaneously provided on the accelerometer output 832.

FIGS. 9A-B are assembled and exploded illustrations, respectively, of a vibration-modulated (vib) physiological sensor embodiment 900 that can be attached to a skin surface proximate various parts of a person's body, such as the chest, ribs, stomach, waist, arms or back so as to, for example, determine respiration-related parameters. In another embodiment, a modulated physiological sensor 900 may have an optical sensor (emitter and detector) combined with the accelerometer and vib. In this manner, the sensor can generate physiological measurements of pulsatile blood flow for blood constituent analysis, physiological measurements of non-pulsatile (venous) blood flow artificially pulsed by the vib and respiration measurements based upon either or both of pleth-modulated optical sensor waveforms and vib-modulated mechanical (accelerometer) waveforms.

Figure 10:
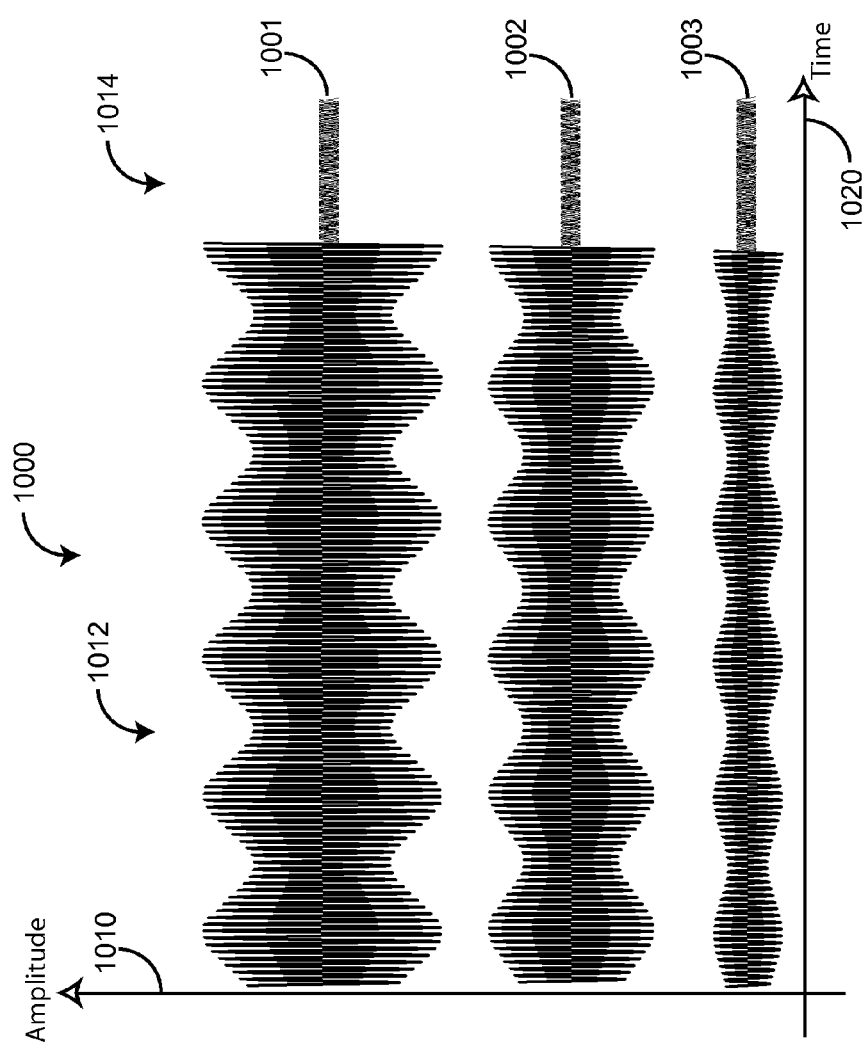
FIG. 10 is a graph of a vibration-accelerometer physiological sensor output versus time illustrating three-axis of respiration envelopes with the vibration turned on and off.

FIG. 10 is a vibration-accelerometer physiological sensor output 1000 illustrating three-axis respiration envelope amplitudes 1010 versus time 1020. The vibration continuously modifies the coupling of the accelerometer to the skin, which effectively multiples the measured acceleration due to respiration by that due to the vibration. This yields AM modulation waveforms 1001-1003 that display a (greatly magnified) respiration envelope. This effect is amply illustrated in comparing the difference in the accelerator response when the vibration (coupling modulator) is turned on 1012 and off 1014.

There are various applications for a modulated physiological sensor, as described above. A chest mounted sensor could monitor for sleep apnea at home, as well as in the hospital for patients receiving narcotics in the general wards. An abdomen-mounted sensor could monitor bowel sounds to give a quantifiable measurement to peristalsis. A dual sensor configuration, with one sensor mounted on the upper part of the abdomen and one on the lower part, is used for diagnosing bowel obstruction, small bowel volvulus or intussuception. A sensor mounted over the radial artery would yield a semi-continuous blood pressure measurement. Another configuration is a screening tool for sub-clinical stenosis of major vessels. For example, rather than placing a stethoscope over the carotid arteries or the abdomen to listen to flow through the aorta, a modulated sensor could give a more quantifiable measurement of stenosis, one level better than auscultation but one level below imaging. Another application is the differential diagnosis of heart murmurs aided by noise cancellation of breathing and other mechanical movements so as to distinguish distinctive murmur patterns (e.g. crescendo/decrescendo).

A modulated physiological sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A modulated physiological sensor for determining a physiological parameter, the modulated physiological sensor comprising:
    an accelerometer coupled with a surface area of a skin of a living being, said accelerometer configured to detect a physiological signal responsive to a physiological process of the living being, wherein the physiological process comprises a respiration process;
    an emitter that emits light towards the surface area of the skin of the living being;
    a detector that detects the emitted light after attenuation from the skin of the living being, the detector having a cutoff frequency;
    a first modulator that varies a coupling of the detector to the surface area at a first modulation frequency greater than the cutoff frequency, thereby at least modulating the detected light attenuation signal at the first modulation frequency greater than the cutoff frequency;
    a second modulator that provides an active pulsation to the skin of living being, wherein the accelerometer, the emitter, the detector, the first modulator, and the second modulator are mounted on a single substrate; and
    a monitor that controls the first modulator to generate physiological measurement of pulsatile blood flow for blood constituent analysis and the physiological signal from the accelerator and controls the second modulator to generate physiological measurement of non-pulsatile blood flow.

2. The modulated physiological sensor according to claim 1 wherein the first modulator comprises a vibration element.

3. The modulated physiological sensor according to claim 2 further comprising a detector substrate that co-mounts the detector and the vibration element.

4. The modulated physiological sensor according to claim 3 further comprising an attachment that releasably affixes the detector substrate, the detector and the vibration element to the surface area.

5. The modulated physiological sensor according to claim 4 wherein the monitor further detects direction and type of propagations from at least one of X, Y, and Z axis components detected from the accelerometer.

6. The modulated physiological sensor according to claim 5 wherein the vibration element comprises a coin motor.

7. The modulated physiological sensor according to claim 6 wherein the substrate comprises a circuit board that mechanically mounts and electrically interconnects the detector and the coin motor.

8. The modulated physiological sensor according to claim 7 wherein the attachment comprises a tape having a sticky side that attaches to the surface area and a housing side that encloses the circuit board.

* * * * *